United States Patent
Beeckler et al.

(10) Patent No.: US 10,893,902 B2
(45) Date of Patent: *Jan. 19, 2021

(54) INTEGRATED RESISTIVE FILTERS IN CATHETER DISTAL END

(71) Applicant: BIOSENSE WEBSTER (ISRAEL) LTD., Yokneam (IL)

(72) Inventors: Christopher Thomas Beeckler, Brea, CA (US); Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 174 days.

This patent is subject to a terminal disclaimer.

(21) Appl. No.: 15/793,411

(22) Filed: Oct. 25, 2017

(65) Prior Publication Data

US 2019/0117297 A1    Apr. 25, 2019

(51) Int. Cl.
| | |
|---|---|
| A61B 18/14 | (2006.01) |
| A61N 1/08 | (2006.01) |
| A61B 5/055 | (2006.01) |
| A61B 5/042 | (2006.01) |
| A61N 1/37 | (2006.01) |
| A61N 1/06 | (2006.01) |
| A61B 5/027 | (2006.01) |

(52) U.S. Cl.
CPC ........ *A61B 18/1492* (2013.01); *A61B 5/0422* (2013.01); *A61B 5/055* (2013.01); *A61N 1/086* (2017.08); *A61N 1/3718* (2013.01); *A61B 5/027* (2013.01); *A61B 2562/166* (2013.01); *A61N 1/06* (2013.01); *A61N 1/08* (2013.01)

(58) Field of Classification Search
CPC ... A61B 18/1492; A61B 5/0422; A61B 5/055; A61B 5/027; A61N 1/06; A61N 1/08
See application file for complete search history.

(56) References Cited

U.S. PATENT DOCUMENTS

| | | |
|---|---|---|
| 5,391,199 A | 2/1995 | Ben-Haim |
| 6,239,724 B1 | 5/2001 | Doron et al. |
| 6,332,089 B1 | 12/2001 | Acker et al. |
| 6,484,118 B1 | 11/2002 | Govari |

(Continued)

FOREIGN PATENT DOCUMENTS

| | | |
|---|---|---|
| WO | WO 96/05768 A1 | 2/1996 |
| WO | WO 00/28895 A1 | 5/2000 |
| WO | WO 2016/065337 A1 | 4/2016 |

OTHER PUBLICATIONS

International Search Report dated Feb. 5, 2019, International Application No. PCT/US2018/055126.

*Primary Examiner* — Linda C Dvorak
*Assistant Examiner* — Annabeth E Rodriguez (57) ABSTRACT

A distal-end assembly of a medical device, the distal-end assembly includes a flexible substrate and electrical conductors. The flexible substrate is configured to be coupled to a distal end of an insertion tube. The electrical conductors are disposed on the flexible substrate and are shaped to form: (i) one or more electrodes, configured to exchange electrical signals with a proximal end of the medical device, and (ii) one or more printed filters shaped to form at least a resistor, which are disposed adjacently to at least one of the electrodes and are configured to filter signals in a predefined frequency range from the electrical signals exchanged between the at least one of the electrodes and the proximal end.

20 Claims, 4 Drawing Sheets

(56) References Cited

U.S. PATENT DOCUMENTS

| | | |
|---|---|---|
| 6,618,612 B1 | 9/2003 | Acker et al. |
| 6,690,963 B2 | 2/2004 | Ben-Haim et al. |
| 2002/0065455 A1 | 5/2002 | Ben-Haim et al. |
| 2003/0120150 A1 | 6/2003 | Govari |
| 2004/0068178 A1 | 4/2004 | Govari |
| 2008/0119919 A1 | 5/2008 | Atalar et al. |
| 2010/0106214 A1 | 4/2010 | Min |
| 2010/0331940 A1* | 12/2010 | Indravudh ............... A61N 1/05 607/126 |
| 2011/0009926 A1* | 1/2011 | Lin ............... A61N 1/08 607/60 |
| 2014/0024909 A1* | 1/2014 | Vij ............... A61B 5/055 600/373 |
| 2014/0163546 A1* | 6/2014 | Govari ............... A61B 18/1492 606/34 |
| 2014/0357956 A1* | 12/2014 | Salahieh ............... A61B 5/01 600/160 |
| 2015/0366508 A1 | 12/2015 | Chou et al. |

\* cited by examiner

INTEGRATED RESISTIVE FILTERS IN CATHETER DISTAL END

CROSS-REFERENCE TO RELATED APPLICATIONS

This application is related to a U.S. Patent Application entitled "Integrated LC Filters In Catheter Distal End," Ser. No. 15/793,126, filed Oct. 25, 2017, whose disclosure is incorporated herein by reference.

FIELD OF THE INVENTION

The present invention relates generally to medical devices, and particularly to filters integrated in catheter distal ends for canceling interference.

BACKGROUND OF THE INVENTION

In various medical procedures, a medical tool is inserted into a patient body, which is simultaneously scanned using an anatomical imaging system such as a magnetic resonance imaging (MRI) system. The medical tool may comprise electrodes used to carry out the procedure. Various techniques for producing catheter electrodes operative in MRI environments are known in the art.

For example, U.S. Patent Application Publication 2015/0366508 describes a flex-PCB catheter device that is configured to be inserted into a body lumen. The flex-PCB catheter comprises an elongate shaft, an expandable assembly, a flexible printed circuit board (flex-PCB) substrate, a plurality of electronic components and a plurality of communication paths.

U.S. Patent Application Publication 2014/0024909 describes an MRI-compatible catheter that includes a shaft having opposite distal and proximal end portions. One or more RF tracking coils are positioned adjacent the distal end portion and each includes a conductive lead that electrically connects the RF tracking coil to an MRI scanner. The catheter includes one or more sensing electrodes at the shaft distal end portion, each electrically connected to a resistor having high impedance.

SUMMARY OF THE INVENTION

An embodiment of the present invention that is described herein provides a distal-end assembly of a medical device, the distal-end assembly includes a flexible substrate and electrical conductors. The flexible substrate is configured to be coupled to a distal end of an insertion tube. The electrical conductors are disposed on the flexible substrate and are shaped to form: (i) one or more electrodes, configured to exchange electrical signals with a proximal end of the medical device, and (ii) one or more printed filters shaped to form at least a resistor, which are disposed adjacently to at least one of the electrodes and are configured to filter signals in a predefined frequency range from the electrical signals exchanged between the at least one of the electrodes and the proximal end.

In some embodiments, the predefined frequency range includes at least part of a radio frequency (RF) frequency range. In other embodiments, the signals filtered in the predefined frequency range are caused by a magnetic resonance imaging (MRI) system. In yet other embodiments, the flexible substrate includes a flexible printed circuit board (PCB).

In an embodiment, the flexible substrate is configured to wrap around the distal end of the insertion tube. In another embodiment, one or more of the printed filters are coupled to at least one of the electrodes. In yet another embodiment, at least one of the printed filters is configured to pass electrical signals sensed, from tissue of a patient, by at least one of the electrodes.

In some embodiments, at least one of the printed filters is configured to pass ablation signals to be applied to a patient tissue. In other embodiments, the predefined frequency range includes 58 MHz-70 MHz.

In an embodiment, the one or more printed filters are made from one or more materials selected from a list consisting of an alloy comprising nickel and chromium, an alloy comprising copper and nickel, and titanium. In another embodiment, at least one of the printed filters is configured to reduce one or more of: heating in the medical device, artifacts in an image acquired using the medical device, and interference of the filtered signals with the electrical signals exchanged between the at least one of the electrodes and the proximal end.

There is additionally provided, in accordance with an embodiment of the present invention, a method for producing a distal-end assembly of a medical device, the method includes disposing on a flexible substrate, first electrical conductors shaped to form one or more electrodes for exchanging electrical signals with a proximal end of the medical device. One or more second electrical conductors are disposed adjacently to at least one of the electrodes. The second electrical conductors are shaped to form one or more printed filters including at least a resistor designed for filtering signals in a predefined frequency range from the electrical signals exchanged between the at least one of the electrodes and the proximal end. The flexible substrate is coupled to a distal end of an insertion tube.

There is further provided, in accordance with an embodiment of the present invention, a distal-end assembly of a medical device, the distal-end assembly includes a flexible substrate and electrical conductors. The flexible substrate is configured to be coupled to a distal end of an insertion tube. The electrical conductors are disposed on the flexible substrate and are shaped to form: (i) one or more electrodes, configured to exchange electrical signals with a proximal end of the medical device, and (ii) one or more printed filters, which are disposed adjacently to at least one of the electrodes and are configured to filter signals in a predefined frequency range from the electrical signals exchanged between the at least one of the electrodes and the proximal end.

In some embodiments, at least one of the printed filters is shaped to form at least one of an inductor and a capacitor. In other embodiments, the inductor and the capacitor are connected in parallel. In yet other embodiments, the predefined frequency range includes at least part of a radio frequency (RF) frequency range.

In an embodiment, the signals filtered in the predefined frequency range are caused by a magnetic resonance imaging (MRI) system. In another embodiment, the flexible substrate includes a flexible printed circuit board (PCB). In yet another embodiment, the flexible substrate is configured to wrap around the distal end of the insertion tube.

In some embodiments, one or more of the printed filters are coupled to at least one of the electrodes. In other embodiments, at least one of the printed filters is configured to pass ablation signals to be applied to a patient tissue.

In an embodiment, the predefined frequency range includes 58 MHz-70 MHz. In another embodiment, at least one of the printed filters is configured to reduce one or more of: heating in the medical device, artifacts in an image acquired using the medical device, and interference of the filtered signals with the electrical signals exchanged between the at least one of the electrodes and the proximal end.

There is additionally provided, in accordance with an embodiment of the present invention, a method for producing a distal-end assembly of a medical device, the method includes disposing on a flexible substrate, first electrical conductors shaped to form one or more electrodes for exchanging electrical signals with a proximal end of the medical device. One or more second electrical conductors are disposed adjacently to at least one of the electrodes. The second electrical conductors are shaped to form one or more printed filters designed for filtering signals in a predefined frequency range from the electrical signals exchanged between the at least one of the electrodes and the proximal end. The flexible substrate is coupled to a distal end of an insertion tube.

The present invention will be more fully understood from the following detailed description of the embodiments thereof, taken together with the drawings in which:

DETAILED DESCRIPTION OF EMBODIMENTS

Overview

Some medical procedures involve real-time anatomical imaging, carried out, for example, using a magnetic resonance imaging (MRI) system. Medical devices that may be used simultaneously with the imagining, may comprise catheters having electrodes used, for example, for conducting electrical signals to or from patient tissue.

The MRI system applies a pulsed radiofrequency (RF) field to change the orientation of a magnetic field in tissue, resulting in induction of a signal at a specific frequency in an antenna (receiver coil). The frequency required to elicit a response from the tissue magnetization is dependent on the field strength of the externally applied magnetic field. For example, at a magnetic field of 1.5 tesla, the RF frequency is about 64 MHz. Unless accounted for, the RF field of the MRI system may induce undesired RF signals in the catheter wiring and/or electrodes, thereby distorting the desired signals of the catheter, creating image artifacts on the MRI scan, and undesirable heating along the catheter.

Embodiments of the present invention that are described hereinbelow provide catheters adapted to operate in MRI environment. Specifically, the catheter comprises filters for canceling RF interference caused by the MRI system, which interference may interfere with electrical signals of the electrodes. Methods for producing catheters with integrated filters are presented below as well.

In some embodiments, a catheter may comprise a distal-end assembly made from a flexible substrate, such as a flexible printed circuit board (PCB) sheet coupled to a distal end of an insertion tube.

In some embodiments, electrical traces are disposed on the PCB sheet in suitable patterns to form the electrodes, as well as filters that are designed to cancel interference caused to the electrodes due to the activity of the MRI system.

The electrodes are configured to exchange electrical signals with a proximal end of the catheter, and the filters are formed adjacently to the electrodes and are configured to filter out the RF signals that interfere with the exchanged electrical signals.

In some embodiments, the electrodes are configured to sense electrical signals from a patient heart, in which case the filter comprises a resistor. In other embodiments, the electrodes are configured to apply ablation signals to tissue of the patient heart, and the filter comprises an inductor L and a capacitor C interconnected in parallel, in an LC circuit configuration.

In some embodiments, the electrodes and filters are produced using very large scale integration (VLSI) processes. In an embodiment, the electrical traces are formed by depositing one or more conductive layers on an outer surface of the PCB sheet, for example by using one or more physical vapor deposition (PVD) processes.

In an embodiment, the deposited conductive layers are shaped to form the electrodes and filters using suitable patterning processes, such as lithography and etching. Subsequently, the distal-end assembly is produced by wrapping the PCB sheet around the insertion tube.

The disclosed techniques help to improve the functionality of medical catheters to carry out complicated life-saving procedures, such as electrophysiological (EP) mapping and tissue ablation, simultaneously with advanced imaging procedures such as MRI.

The disclosed techniques enable customizing the characteristics of the filters integrated into the distal end of the catheter by forming suitable circuits on the PCB sheet, e.g., using VLSI processes. For example, to filter out a first frequency range the filter may comprise a single resistor, whereas to filter out a second frequency range the filter may comprise a parallel LC circuit.

System Description

Figure 1:
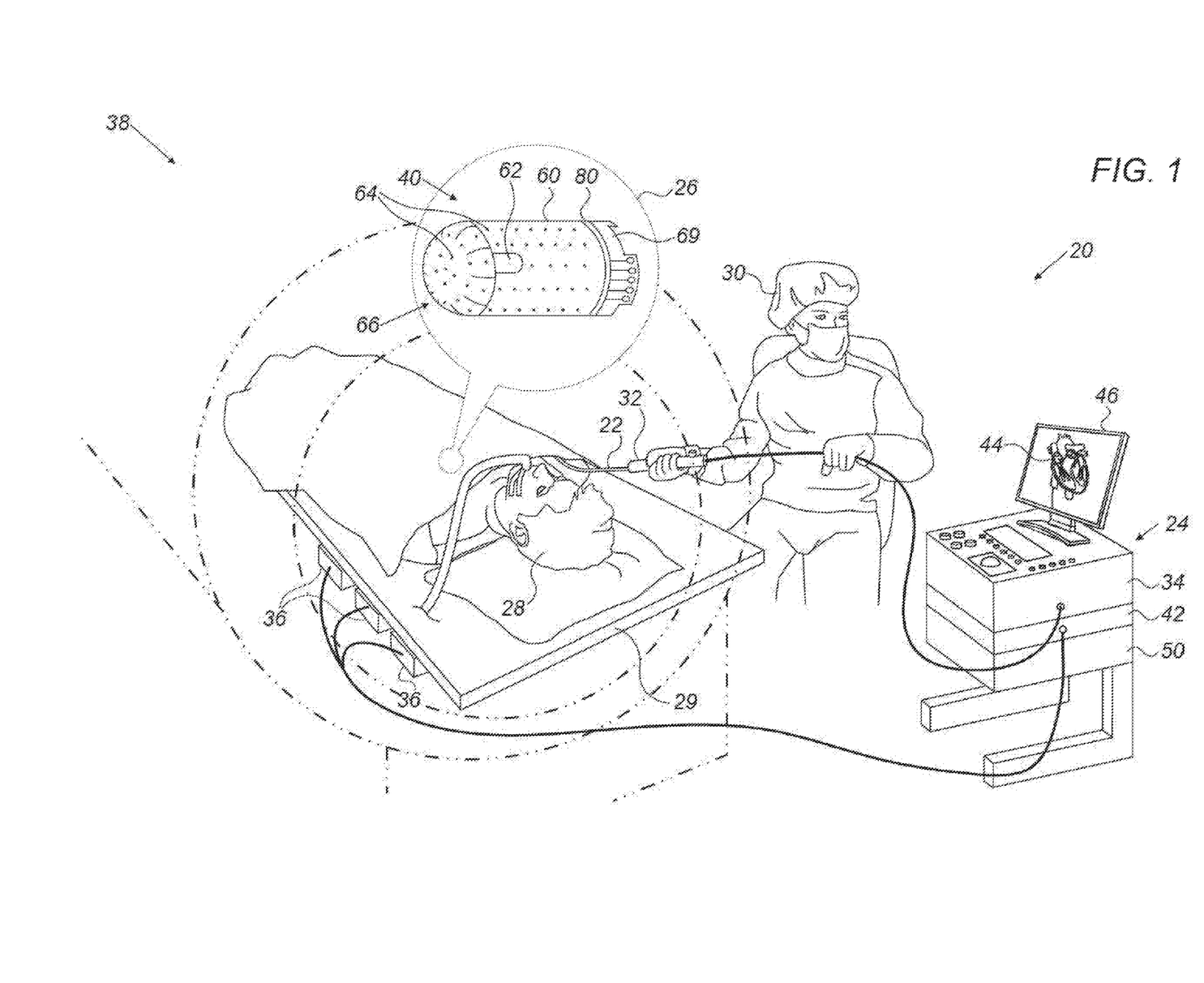
FIG. 1 is a schematic, pictorial illustration of a catheterization system, in accordance with an embodiment of the present invention.

FIG. 1 is a schematic, pictorial illustration of a catheterization system 20, in accordance with an embodiment of the present Invention. System 20 comprises a medical device, such as a probe, in the present example a cardiac catheter 22, and a control console 24. In the embodiment described herein, catheter 22 may be used for any suitable therapeutic and/or diagnostic purposes, such as ablating tissue or sensing electrophysiological (EP) signals from a heart (not shown) of a patient 28.

In some embodiments, system 20 comprises a magnetic resonance imaging (MRI) system 38, which is configured to produce anatomical images of patient tissue. In some embodiments, MRI system 38 comprises magnetic field coils (not shown), comprising field gradient coils, which together generate a spatially variant magnetic field.

The spatially variant magnetic field provides spatial localization for radio frequency (RF) signals generated in the system. In some embodiments, MRI system 38 produces RF signals at a frequency of about 64 mega-hertz (MHz), or any other suitable range of RF frequencies.

In addition, MRI system 38 comprises transmitting and receiving coils (not shown). In a transmit mode the transmitting coils radiate RF pulsed energy to patient 28, the RF pulses of energy interacting with the nuclear spins of the patient tissue and thereby realigning the magnetic moments of the nuclei away from their equilibrium positions. In a receive mode, the receiving coils detect RF signals received from the patient's tissue as the tissue nuclei relax to their equilibrium state.

In some embodiments, console 24 comprises a processor 34, typically a general-purpose computer, with suitable front end and interface circuits for receiving signals from MRI system 38 and from catheter 22, and for controlling other components of system 20.

In some embodiments, console 24 further comprises a memory 50 and a display 46, which is configured to display data, such as an image 44 of at least part of the heart of patient 28. In some embodiments, image 44 may be acquired using MRI system 38, or using any other suitable anatomical imaging system.

A physician 30 (such as an interventional cardiologist) inserts catheter 22 through the vascular system of patient 28 lying on a table 29. Catheter 22 comprises a distal-end assembly 40, shown in an inset 26 and depicted in details in FIGS. 2 and 5 below. Physician 30 moves assembly 40 in the vicinity of the target region in the heart by manipulating catheter 22 with a manipulator 32 near the proximal end of catheter 22. The proximal end of catheter 22 is connected to interface circuitry in processor 34.

In some embodiments, the position of distal-end assembly 40 in the heart cavity is typically measured using position sensing techniques. This method of position sensing is implemented, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

In some embodiments, console 24 comprises a driver circuit 42, which drives magnetic field generators 36 placed at known positions external to patient 28 lying on table 29, e.g., below the patient's torso.

Reference is now made to inset 26. In some embodiments, distal-end assembly 40 comprises a flexible printed circuit board (PCB) sheet 60, wrapped around an internal member 69 depicted in detail in FIG. 5 below. The internal member is also referred to herein as an insertion tube.

In some embodiments, assembly 40 further comprises a dome-cover 66, which is fabricated from a flexible PCB and configured to wrap around a ring-shaped dome-support (shown in FIG. 5 below) using any suitable coupling technique.

In some embodiments, PCB sheet 60 and/or dome-cover 66 may be perforated so as to form one or more irrigation holes 64, which are configured to allow irrigation fluid to flow out from the insertion tube when irrigating the tissue of the heart, for example during an ablation procedure.

In some embodiments, assembly 40 further comprises one or more micro-electrodes 62 and a ring electrode 80, which are configured to exchange electrical signals with the proximal end of catheter 22 and to conduct the electrical signals to or from the tissue of the heart. During a medical procedure, such as cardiac EP mapping or tissue ablation, micro-electrodes 62 and ring electrode 80 are brought into contact with the tissue of the heart, so as to sense electrical signals originated therefrom, or to apply ablation signals for ablating the tissue as will be described below.

In the context of the present disclosure and in the claims, the terms "electrode" and "micro-electrode" are used interchangeably and refer to sensing electrodes or to ablating electrodes configured to sense electrical signals from the heart or to ablate tissue of the heart, respectively.

In some embodiments, ring electrode 80 may be used for sensing electrocardiogram (ECG) signals or any other type of signals from the heart of patient 28. Note that the description below mainly refers to micro-electrodes 62, but is also applicable for ring electrode 80.

In some embodiments, micro-electrodes 62 are coated with a conductive layer (made from, e.g., gold, or any other suitable material), configured to transfer the electrical signals to/from the tissue of the heart, at a predefined frequency range.

In some embodiments, assembly 40 may be used for ablating tissue of the heart. In some embodiments, during the ablation, micro-electrodes 62 are configured to transfer to the tissue electrical signals at a given frequency range.

In some embodiments, the conductive layer of micro-electrodes 62 is typically deposited on an outer surface of PCB sheet 60. In other embodiments, the conductive layer may be deposited on dome-cover 66 in addition to, or instead of on PCB sheet 60.

As described above, MRI system 38 produces RF signals, e.g., at a predefined frequency of 64 MHz, that may interfere with the electrical signals exchanged between micro-electrodes 62 and the proximal end of catheter 22, cause image artifacts (e.g., in image 44), and undesirable heating along the catheter.

In some embodiments, one or more filters (shown in FIGS. 2-4 below) are disposed (e.g., printed) on PCB sheet 60 adjacently to at least one of micro-electrodes 62. Typically, each electrode is associated with one or more respective filters.

In an embodiment, the filters are configured to filter a predefined frequency range from interfering with the electrical signals exchanged between the respective micro-electrodes and the proximal end. In some embodiments, the frequency range may comprise a frequency of about 64 MHz produced by MRI system 38 that has a magnetic field strength of 1.5 tesla. An example method for producing distal-end assembly 40 and further details regarding the filters are depicted in details in FIGS. 2-6 below.

In some embodiments, the filters and other components of the catheter, such as one or more thermocouples (not shown), may be produced between the conductive layers of PCB sheet 60 or mounted on the outer surface of PCB sheet 60. Thermocouples can be used for monitoring tissue temperature during the ablation.

In some embodiments, processor 34 typically comprises a general-purpose processor, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

The configuration of distal-end assembly 40 shown in FIG. 1 is an example configuration, which is chosen purely for the sake of conceptual clarity. In alternative embodiments, any other suitable configuration can also be used. For example, the size and shape of distal-end assembly 40, and the number and locations of micro-electrodes 62 and respective filters may be implemented using any suitable components and layout appropriate for conducting a suitable medical procedure on tissue of any organ of patient 28. Furthermore, the flexible substrate used for implementing the distal-end device may comprise any other suitable substrate other than a PCB.

Integrating Filters into the Catheter Distal End

Figure 2:
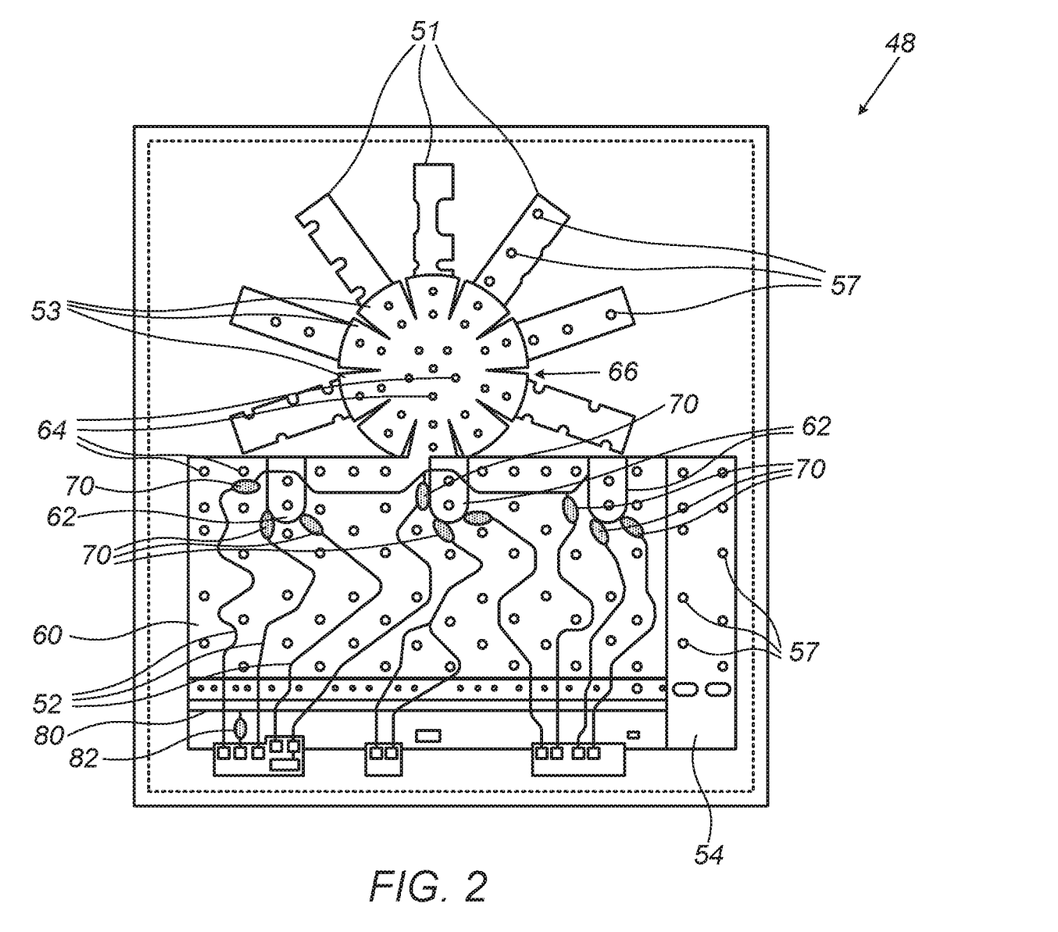
FIG. 2 is a schematic, pictorial illustration of a flexible substrate having electrodes and filters printed thereon, in accordance with an embodiment of the present invention.

FIG. 2 is a schematic, pictorial illustration of a flexible substrate 48, in accordance with an embodiment of the present invention. In some embodiments, substrate 48 comprises a single section that may be used for producing a single unit of distal-end assembly 40. In other embodiments, substrate 48 may comprise one or more substantially similar sections (not shown), used for producing multiple respective units of distal-end assembly 40.

In some embodiments, each section of substrate 48 comprises PCB sheet 60, cover 66 and all other elements of assembly 40 depicted in FIG. 1 above. These embodiments enable high-volume manufacturing (HVM) of assemblies 40 by applying on substrate 48 one set of very large scale integration (VLSI) processes, described with reference to FIG. 1 above, for simultaneously producing multiple sections.

In some embodiments, the VLSI processes may comprise deposition of one or more conductive layers at selected locations on an outer surface of PCB sheet 60, using any suitable process, such as physical vapor deposition (PVD). The deposited conductive layers are shaped to form various components integrated on PCB sheet 60 and dome-cover 66, e.g., using patterning processes, such as lithography and etching.

After concluding the production of the sections, substrate 48 is cut, such that each section is separated from its neighbor sections. In the example of FIG. 2, substrate 48 comprises a single singulated section.

In some embodiments, PCB sheet 60 typically comprises electrical interconnections, such as conductive traces 52, which are configured to electrically connect the electronic devices coupled to substrate 48 to suitable wires that traverse the catheter, and to electrically connect between the proximal end of catheter 22 and electrodes 62.

In some embodiments, one or more filters 70 are printed on PCB sheet 60, adjacently to respective micro-electrodes 62. In some embodiments, filters 70 are configured to filter out interfering signals in a predefined frequency range (e.g., 58 MHz-70 MHz). In an embodiment, filter 70 may comprise an inductor L and a capacitor C interconnected in parallel, in an LC circuit configuration shown in detail in FIG. 3 below. In this embodiment, the LC circuit may serve as a band-stop filter of high impedance signals centered around 64 MHz.

In other embodiments filters 70 uniformly attenuate interfering signals across essentially the entire useful frequency range. In an embodiment, filter 70 may comprise a resistor R coupled to electrode 62 and to trace 52. In this embodiment, resistor R is configured to attenuate currents of all frequencies but low currents, such as pico-ampere (pA) currents, conducted on trace 52. The reduction of high currents reduces image artifacts on the MRI scan (e.g., on image 44), and undesirable heating along catheter 22.

The interfering signals are produced by MRI system 38 and are filtered out so as to reduce or even cancel interferences they may cause to the electrical signals exchanged between micro-electrodes 62 and the proximal end of catheter 22.

Note that the interfering signals, from MRI system 38 or from any other source, may interfere with the intended operation of various components of system 20 and are typically conducted from the blood or tissue to micro-electrodes 62 and into the catheter by traces 52.

In some embodiments, each filter 70 is physically coupled to micro-electrode 62, such that filter 70 is configured to block or sufficiently attenuate any interfering signal in a predefined frequency range (e.g., 58 MHz-70 MHz) that would otherwise be conducted between micro-electrodes 62 and the proximal end of catheter 22, via traces 52.

In some embodiments, a filter 82 is printed on PCB sheet 60, adjacently to ring electrodes 80. Filter 82 is configured to filter out interfering signals in a predefined frequency range (e.g., 58 MHz-70 MHz) so as to reduce the level of noise from the ECG signals sensed by ring electrode 80. In some embodiments, filter 82 may have a structure similar to filter 70 of micro-electrodes 62. In alternative embodiments, filter 82 may have any other suitable structure.

In principle it is possible to block the interfering signals by implementing filters of a predefined frequency range at the proximal end of catheter 22, e.g., at manipulator 32. However, this configuration does not eliminate the heating induced on the wires that span the length of the catheter nor does it address the associated image artifacts. Therefore, the desirable location for disposing the filters so as to block the interfering signals is as close to the respective electrodes (e.g., electrodes 62 and 80) of distal-end assembly 40 as possible.

In some embodiments, micro-electrodes 62 may be used for sensing low-voltage electrical signals from the heart of patient 28, e.g., on the order of 0.01 mV-1 mV. In these embodiments, a first type of filter 70 is suitable for filtering the interfering signals from MRI system 38. In other embodiments, the electrodes are configured to apply ablation, e.g., to the heart tissue, using high-current electrical signals, such as 50 mA-5 A.

In these embodiments, a second type of filter 70, different from the first type is suitable for filtering the interfering signals. Embodiments that employ the first and second types of filters are depicted in detail in FIGS. 3-4 below.

In alternative embodiments, electrodes 62 may conduct any other type of electrical signals to/from any organ of patient 28, in the presence of interfering signals of any frequency-range.

In these embodiments, system 20 may require, for each type of electrical signal, a different type of filter, suitable for blocking interfering signals having a respective frequency-range.

Figure 5:
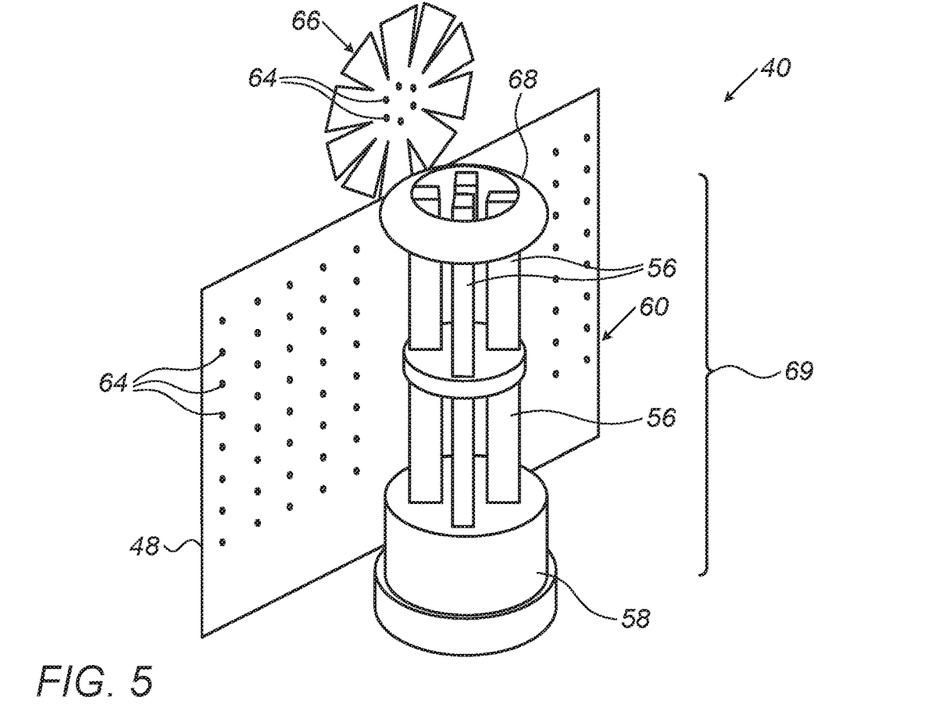
FIG. 5 is a schematic, exploded pictorial illustration of a distal-end assembly of a catheter, in accordance with an embodiment of the present invention.

In an embodiment, irrigation holes 64 are formed in sheet 60 and/or on dome-cover 66, when sheet 60 and cover 66 are in a planar position, before wrapping around member 69 and the ring-shaped dome-support as shown in FIG. 5 below.

In some embodiments, sheet 60 comprises a section 54, which is configured to connect the edges of sheet 60 to one another, when sheet 60 is wrapped around member 69, and to connect between PCB sheet 60 and cover 66, as will be described in FIG. 5 below.

In some embodiments, cover 66 comprises multiple tabs 51, each of which is extended from a respective section 53 of cover 66, and are configured to couple between dome-cover 66 and section 54 of sheet 60.

In some embodiments, section 54 and some of tabs 51 comprise exclusion zone elements 57, which are created in some of tabs 51 so as to not overlap irrigation holes 64 when sheet 60 and cover 66 are in a wrapped position around member 69.

In alternative embodiments, after wrapping, the left and right edges of sheet 60 may be coupled to one another by welding, adhesive, or using any other suitable technique to couple sheet 60 and cover 66 to member 69, and to one another.

In some embodiments, sheet 60 and cover 66 of section 48 are shown in a planar form after concluding the VLSI processes, and before wrapping sheet 60 and cover 66 around member 69 and on the apex of assembly 40, respectively, as will be depicted in detail in FIG. 5 below.

Figure 3:
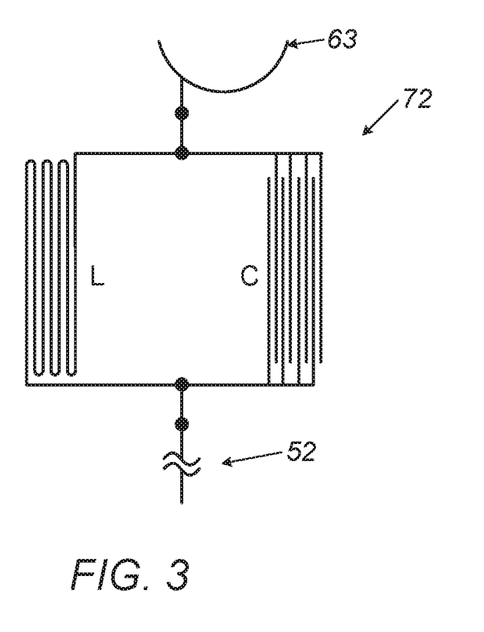
FIGS. 3 and 4 are schematic, pictorial illustrations of filters formed in respective flexible substrates, in accordance with embodiments of the present invention.

FIG. 3 is a schematic, pictorial illustration of filters 72 and ablation electrodes 63 formed on PCB sheet 60, in accordance with an embodiment of the present invention. Filters 72 and ablation electrodes 63 may respectively replace, for example, filters 70 and electrodes 62 of FIG. 2 above.

In other embodiments, electrodes 63 and filters 72 may be formed in cover 66, in addition to, or instead of being formed on PCB sheet 60.

The process depicted hereinbelow is suitable for producing electrodes 63 and filters 72 in sheet 60 and/or in cover 66.

In some embodiments, electrodes 63 are delivering currents and configured to conduct ablation signals from the proximal end of catheter 22 to the heart tissue of patient 28. In some embodiments, filters 72 are configured to pass ablation signals, e.g., from the proximal end of catheter 22, to electrodes 63 for ablating the patient tissue.

In an embodiment, filter 72 comprises a parallel LC circuit comprising an inductor L and a capacitor C connected in parallel. In the example of FIG. 3, one terminal of filter 72 is coupled to trace 52 and the other terminal of the filter is coupled to electrode 63, similar to the interconnection configuration of filter 70 in FIG. 2 above.

In some embodiments, inductor L and capacitor C are made from one or more conductive layers of electrical traces of preferably gold or copper deposited on PCB sheet 60 using a PVD process or any other suitable process. The conductive layers are deposited in a suitable shape to form the components comprising filter 72, e.g., using lithography and etching processes.

In some embodiments, inductor L and capacitor C of filter 72 may be patterned using a single mask configured to pattern other components of PCB sheet 60, such as traces 52 and electrodes 63.

In other embodiments, filter 72 may be formed using any other suitable sequence of deposition and patterning processes, such as using separate lithography mask and patterning process.

In some embodiments, filter 72 is configured to filter signals in a predefined frequency range from being coupled onto trace 52 causing catheter heating and image artifacts. In these embodiments, the frequency of the interfering signals comprises the 64 MHz frequency produced by 1.5T MRI system 38. In the case of a different magnetic field strength the corresponding Larmor frequency would be used.

In some embodiments, the configuration of filter 72 is suitable for filtering signals from interfering with the ablation signals having typical currents values of 50 mA to 5 A and frequency range of 50 kHz to 25 MHz.

Note that small values of inductance (e.g. 1 nH to 1000 nH) and capacitance (e.g., 5 pF to 5000 pF) are sufficient for inductor L and capacitor C of filter 72 to attenuate the interfering signals from MRI system 38.

In other embodiments, any other suitable configuration of one or more inductors L, and/or capacitors C, and/or other components, may be arranged to form a filter compatible with any type of electrode formed on substrate 48. Furthermore, each component of filter 72 (e.g., capacitor C) may have any suitable value.

Figure 4:
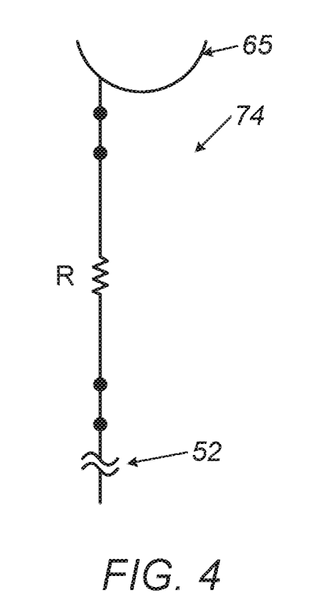

FIG. 4 is a schematic, pictorial illustration of filters 74 and micro-electrodes 65 formed in PCB sheet 60, in accordance with an embodiment of the present invention.

Filters 74 and micro-electrodes 65 may respectively replace, for example, filters 70 and micro-electrodes 62 of FIG. 2 above. In some embodiments, filter 74 comprises a resistor R coupled to electrode 65 and to trace 52.

In some embodiments, micro-electrodes 65 are non-current carrying electrodes configured to sense electrical signals from the tissue of the heart of patient 28. In the example of system 20, the electrical signals sensed by micro-electrodes 65 have a current range of 1 pA-1 µA, and a frequency range of 0.01-1000 Hz.

In some embodiments, filter 74 is configured to filter a predefined frequency range from interfering with the electrical signals of the heart tissue that are sensed by micro-electrodes 65. In some embodiments, filter 74 is further configured to pass the electrical signals of the heart tissue that are sensed by micro-electrodes 65 and conducted, via traces 52, to processor 34.

Note that each filter 74 is formed with close proximity (e.g., a few millimeters or even physically coupled) to a respective micro-electrode 65 so as to filter the aforementioned interfering signals. The interfering signals may be produced by MRI system 38 or by any other source.

In some embodiments, resistor R is formed by patterning a suitable resistive layer between trace 52 and micro-electrode 65. For example, resistor R may be formed by shaping the width of a section of trace 52 to be narrowed in proximity to micro-electrode 65. In this configuration, the section of trace 52 having a thinner width may have higher a resistance compared to the other sections of traces 52, thereby may attenuate or completely block the interfering signals from interfering with the heart signals sensed by micro-electrode 65.

In other embodiments, resistor R may be made from a material other than the material from which traces 52 are made, having a higher inherent resistance compared to the material of traces 52, such as nichrome (an alloy comprising nickel and chromium), constantan (an alloy comprising copper and nickel), titanium, or any other suitable material.

In other embodiments, resistor R may be made by either depositing less conductive material to make a feature which has lower thickness of material thickness, or by selectively removing material leaving a thinner layer of material behind.

In other embodiments, any suitable combination of the techniques described above may be applied so as to provide the desired resistance of resistor R. For example, a narrow and thin feature may be formed out of a material having higher inherent resistance.

The configuration of filters 72 and 74 shown in FIGS. 3 and 4 above are depicted purely by way of example. In alternative embodiments, substrate 48 of distal-end assembly 40 may comprise any other types and configurations of filters suitable for filtering any predefined frequency range of interfering signals. The characteristics of such filters are defined by the types and arrangements of such components (e.g., combinations of RLC or RC circuits) and the characteristics of each component of the filter.

FIG. 5 is a schematic, exploded pictorial illustration of distal-end assembly 40, in accordance with an embodiment of the present invention. FIG. 5 shows the opposite surfaces of sheet 60 and cover 66 from those shown in FIG. 2 above.

In some embodiments, internal member 69 of distal-end assembly 40 may be made of plastic or any other suitable material. Member 69 may have a skeleton support structure, as shown in FIG. 5, or any other suitable structure.

A base 58 is located at the proximal end of member 69, a ring-shaped dome-support 68 is located at the apex of member 69, and multiple ribs 56 connect the base and the dome-support. In this embodiment, member 69 has an internal lumen for directing irrigation into the inside of cavity formed by flexible PCB sheet 60.

In some embodiments, dome-cover 66 may be glued to dome-support 68, or coupled thereto using the configuration depicted in FIG. 2 above. In alternative embodiments, cover 66 may be fabricated from a liquid crystal polymer (LCP) PCB, which may be formed (e.g., thermoformed) into a cup shape and bonded to sheet 60. The cup shape may be bonded to dome-support 68 and sheet 60 bonded to base 58 using any suitable bonding technique known in the art.

In some embodiments, sheet 60 and cover 66 are made from a single piece of contiguous PCB or any other suitable flexible substrate. In alternative embodiments, sheet 60 and cover 66 may be formed from separate pieces of material and coupled to one another using welding or any other suitable coupling technique.

Figure 6:
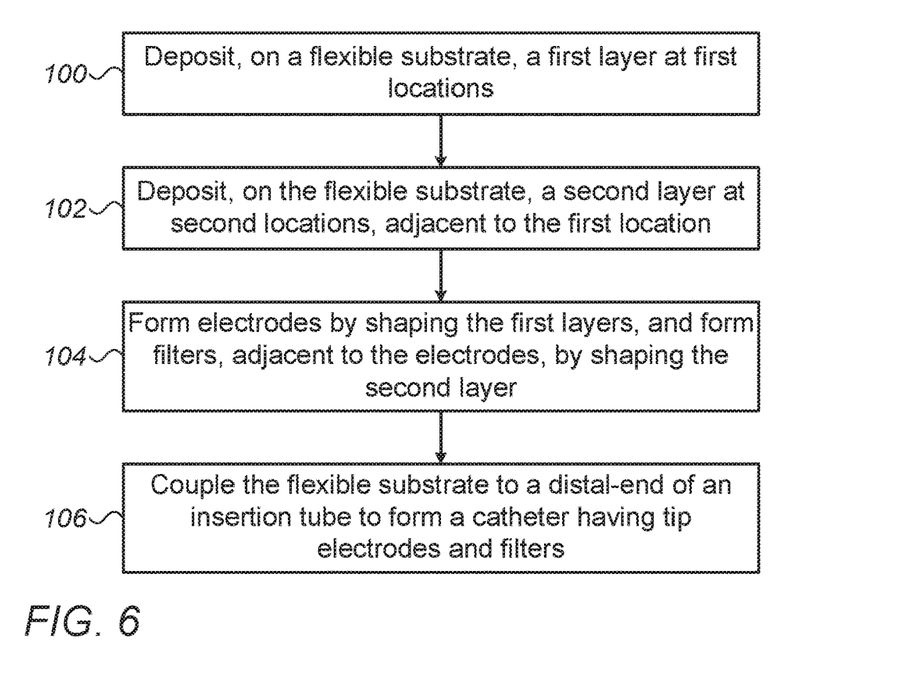
FIG. 6 is a flow chart that schematically illustrates a method for producing a catheter comprising electrodes and filters integrated on a flexible substrate, in accordance with an embodiment of the present invention.

FIG. 6 is a flow chart that schematically illustrates a method for producing distal-end assembly 40, in accordance with an embodiment of the present invention. The method begins with depositing a first conductive layer on first selected locations of flexible substrate 48, at a first deposition step 100.

At a second deposition step 102, a second conductive layer is deposited on flexible substrate 48 at second selected locations that are adjacent to the first selected locations. In some embodiments, the first and second conductive layers are made from the same material, such as gold or any other suitable material.

In these embodiments, the first and second conductive layers may be deposited simultaneously, so that steps 100 and 102 are carried out as a single deposition step. In other embodiments, the first and second conductive layers are made from different respective materials and are typically deposited at different process steps.

In some embodiments, the first conductive layer is deposited across the entire surface of substrate 48, and subsequently patterned so as to retain only parts of the first conductive layer on the first selected locations of flexible substrate 48. Likewise, the second conductive layer may be deposited across the entire surface of substrate 48, and subsequently patterned so as to retain only parts of the second conductive layer on the second selected locations of flexible substrate 48.

After concluding step 102, the first and second conductive layers are deposited adjacent to one another, typically, in a physical contact with one another.

At a patterning step 104, the first conductive layer is shaped so as to form electrodes, such as micro-electrodes 62, and the second conductive layer is shaped so as to form filters, such as filters 70. In an embodiment, the shaping of the first and second conductive layers is carried out using a single patterning process.

In this embodiment, the patterning process may comprise using a single mask that defines the shapes of micro-electrodes 62 and filters 70, followed by one or more etching steps configured to transfer the shapes defined by the mask.

In alternative embodiments, the process sequence described in steps 100, 102 and 104 may comprise depositing the first conductive layer and patterning the shape of micro-electrodes 62 using a first mask, and subsequently depositing the second conductive layer and patterning the shape of filters 70 using a second mask.

The description of the processes in steps 100, 102, and 104 above is simplified for the sake of clarity, and these example steps are depicted purely by way of example. In alternative embodiments, any other suitable process may be used to produce micro-electrodes 62 and filters 70 adjacent to, or coupled to one another.

In some embodiments, at least one of the first and second conductive layers may comprise a multilayered structure, each conductive layer made from at least two types of sublayers.

At a tip formation step 106, substrate 48 is coupled to member 69 using one of the techniques depicted in FIGS. 2 and 5 above. In the example of distal-end assembly 40, flexible PCB sheet 60 is wrapped around base 58 and ribs 56, and dome-cover 66 is wrapped around dome-support 68. In some embodiments, step 106 concludes the method and enables the formation of distal-end assembly 40.

Although the embodiments described herein mainly address mapping and treatment of cardiac arrhythmias, the methods and systems described herein can also be used in other applications, such as in otolaryngology or neurology procedures.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A distal-end assembly of a medical device, the distal-end assembly comprising:
   a flexible substrate, which is configured to be coupled to a distal end of an insertion tube, the flexible substrate includes a dome cover in the form of a circular sheet connected to a rectangular sheet and a plurality of irrigation holes formed in the flexible substrate; and
   electrical conductors, which are disposed on the flexible substrate and are shaped to form:
   (i) a plurality of micro electrodes disposed along a length of the rectangular sheet adjacent to the dome cover, each electrode configured to exchange electrical signals with a proximal end of the medical device, and
   (ii) (ii) one or more printed filters shaped to form at least a resistor, which are disposed adjacently to each of the plurality of micro electrodes and are configured to filter signals in a predefined frequency range from the electrical signals exchanged between each of the plurality of micro electrodes and the proximal end of the medical device.

2. The distal-end assembly according to claim 1, wherein the predefined frequency range comprises at least part of a radio frequency (RF) frequency range.

3. The distal-end assembly according to claim 1, wherein the signals filtered in the predefined frequency range are caused by a magnetic resonance imaging (MRI) system.

4. The distal-end assembly according to claim 1, wherein the flexible substrate comprises a flexible printed circuit board (PCB).

5. The distal-end assembly according to claim 1, wherein the flexible substrate is configured to wrap around the distal end of the insertion tube.

6. The distal-end assembly according to claim 1, wherein one or more of the printed filters are coupled to at least one of the plurality of miceo electrodes.

7. The distal-end assembly according to claim 1, wherein at least one of the printed filters is configured to pass electrical signals sensed, from tissue of a patient, by at least one of the plurality of micro electrodes.

8. The distal-end assembly according to claim 1, wherein at least one of the printed filters is configured to pass ablation signals to be applied to a patient tissue.

9. The distal-end assembly according to claim 1, wherein the predefined frequency range comprises 58 MHz-70 MHz.

10. The distal-end assembly according to claim 1, wherein the one or more printed filters are made from one or more materials selected from a list consisting of an alloy comprising nickel and chromium, an alloy comprising copper and nickel, and titanium.

11. The distal-end assembly according to claim 1, wherein at least one of the printed filters is configured to reduce one or more of: heating in the medical device, artifacts in an image acquired using the medical device, and interference of the filtered signals with the electrical signals exchanged between the at least one of the electrodes and the proximal end.

12. A method for producing a distal-end assembly of a medical device, the method comprising:
providing a flexible substrate that includes a dome cover in the form of a circular sheet connected to a rectangular sheet and a plurality of irrigation holes formed in the flexible substrate
disposing on the rectangular sheet of the flexible substrate adjacent the circular sheet, first electrical conductors shaped to form a plurality of micro electrodes for exchanging electrical signals with a proximal end of the medical device
disposing on a length of the rectangular sheet opposite the circular sheet an electrode that extends along the length of the rectangular sheet to define a ring electrode;
disposing adjacently to at least one of the plurality of micro electrodes, one or more second electrical conductors shaped to form one or more printed filters comprising at least a resistor designed for filtering signals in a predefined frequency range from the electrical signals exchanged between each of the plurality of micro electrodes and the proximal end; and
coupling the flexible substrate to a distal end of an insertion tube.

13. The method according to claim 12, wherein the predefined frequency range comprises at least part of a radio frequency (RF) frequency range.

14. The method according to claim 12, wherein the signals filtered in the predefined frequency range are caused by a magnetic resonance imaging (MRI) system.

15. The method according to claim 12, wherein disposing on the flexible substrate comprises disposing on a flexible printed circuit board (PCB).

16. The method according to claim 12, wherein coupling the flexible substrate comprises wrapping the flexible substrate around the distal end of the insertion tube.

17. The method according to claim 12, wherein disposing the one or more second electrical conductors comprises coupling one or more of the printed filters to at least one of the plurality of micro electrodes.

18. The method according to claim 12, wherein at least one of the printed filters has a response that passes electrical signals sensed, from tissue of a patient, by at least one of the plurality of micro electrodes.

19. The method according to claim 12, wherein the predefined frequency range comprises 58 MHz-70 MHz.

20. The method according to claim 12, wherein disposing the second electrical conductors comprises reducing one or more of: heating in the medical device, artifacts in an image acquired using the medical device, and interference of the filtered signals with the electrical signals exchanged between the at least one of the plurality of micro electrodes and the proximal end.

* * * * *